US007002011B1

(12) United States Patent
Zindel et al.

(10) Patent No.: US 7,002,011 B1
(45) Date of Patent: Feb. 21, 2006

(54) PROCESS FOR THE PREPARATION OF 2-AMINO-4-CHLORO-1,3,5-TRIAZINES

(75) Inventors: Jürgen Zindel, Bad Sooden-Allendorf (DE); Jens Hollander, Schmitten (DE); Klemens Minn, Hattersheim (DE); Lothar Willms, Hofheim (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/719,508

(22) PCT Filed: Jul. 2, 1999

(86) PCT No.: PCT/EP99/04581

§ 371 (c)(1),
(2), (4) Date: Dec. 12, 2000

(87) PCT Pub. No.: WO00/02868

PCT Pub. Date: Jan. 22, 2000

(30) Foreign Application Priority Data

Jul. 10, 1998 (DE) ................................. 198 30 902

(51) Int. Cl.
C07C 251/18 (2006.01)
(52) U.S. Cl. ...................... 544/204; 544/194; 544/208; 544/209; 544/210; 544/211; 544/212; 544/213
(58) Field of Classification Search ................. 544/216, 544/217, 208, 209, 210, 211, 212, 213, 194, 544/204
See application file for complete search history.

(56) References Cited

U.S. PATENT DOCUMENTS

| 3,361,746 A | 1/1968 | Schmeizer et al. | 260/348 |
| 5,084,570 A | 1/1992 | Burdeska et al. | 544/216 |
| 5,290,754 A | 3/1994 | Nishii et al. | 544/206 |
| 5,403,815 A | 4/1995 | Nishii et al. | 544/207 |
| 6,069,114 A * | 5/2000 | Lorenz et al. | 544/197 |

FOREIGN PATENT DOCUMENTS

| CA | 2081413 | 5/1993 |
| DE | 1 178 437 | 9/1964 |
| DE | 4139624 A1 | 6/1993 |
| EP | 0 810 219 A1 | 12/1997 |
| WO | WO 90/09378 | 8/1990 |
| WO | WO 96/25404 | 8/1996 |
| WO | WO 97/00254 | 1/1997 |
| WO | WO 97/08156 | 3/1997 |
| WO | WO 97/19936 | 6/1997 |
| WO | WO 97/29095 | 8/1997 |
| WO | WO 97/31904 | 9/1997 |
| WO | WO 97/35481 | 10/1997 |
| WO | WO 98/10654 | 3/1998 |
| WO | WO 98/15536 | 4/1998 |
| WO | WO 98/15537 | 4/1998 |
| WO | WO 98/15538 | 4/1998 |
| WO | WO 98/15539 | 4/1998 |
| WO | WO 98/34925 | 8/1998 |

OTHER PUBLICATIONS

Dorn, H., Chapter 3, Formation of Carbon-Halogen Bonds, pp. 102-117, in Preparative Organic Chemistry edited by Hilgetag, G., and Martini A., 1972.*
Chakrabarti et al., Tetrahedron, vol. 31, pp. 1879-1882, 1975.

(Continued)

Primary Examiner—Richard L. Raymond
(74) Attorney, Agent, or Firm—Frommer Lawrence & Haug LLP

(57) ABSTRACT

Compounds of the formula (I) or salts thereof

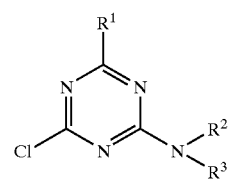

(I)

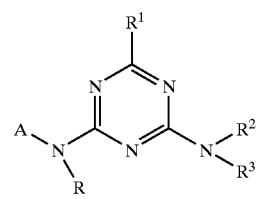

(IV)

are suitable for preparing active substances from the from the class of the aminotriazines of the formula (IV), for example herbicidal active substances. The compounds (I) can be prepared by chlorinating compounds of the formula (II)

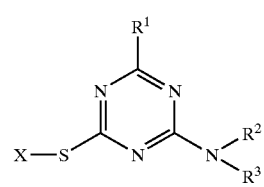

(II)

where, in the formulae, $R^1$, $R^2$, $R^3$ and X are as defined in claim 1 and A and R have the meaning required in the active substances to be prepared, and they can be reacted with amines of the formula A—NH—R to give the active substances.

18 Claims, No Drawings

OTHER PUBLICATIONS

Riley et al., J. Heterocyclic Chem., vol. 23, pp. 1709-1714, 1986.

Eilingsfeld et al., Chem. Ber., vol. 100, pp. 1874-1891, 1967.

Helv. Chim. Acta, vol. 33, pp. 1366-1369, 1950.

Reimschuessel et al., J. Am. Chem. Soc., vol. 82, pp. 3756-3762, 1960 (XP-002119854).

Nishigaki et al., J. Med. Chem., vol. 12, pp. 39-42, 1969.

* cited by examiner

PROCESS FOR THE PREPARATION OF 2-AMINO-4-CHLORO-1,3,5-TRIAZINES

This application is a 371 of PCT/EP99/04581, filed Jul. 2, 1999.

The invention relates to the technical field of the chemical synthesis of bioactive compounds, preferably the processes for the preparation of crop protection agents and intermediates for these processes.

It has been disclosed that 2-amino-4-chloro-1,3,5-triazines which are substituted by organic radicals in the 6-position on the triazine ring can be employed for preparing bioactive aminotriazines, for example herbicidal aminotriazines, the chlorine atom being exchanged for an N-substituted amino radical; cf. WO-A-90/09378, WO-A-96/25404, WO-A-97/00254, WO-A-97/08156, WO-A-97/19936, WO-A-97/29095, WO-A-97/31904, WO-A-97/35481, WO-A-98/10654, WO-A-98/15536, WO-A-98/15537, WO-A-98/15538, WO-A-98/15539; moreover, aminotriazines have been proposed in International Application No. PCT/EP98/00283 and in German Patent Application No. 19826670.7.

The substituted 2-amino-4-chloro-1,3,5-triazines can be obtained in accordance with a known process from the suitably substituted 2,4-dichloro-1,3,5-triazines and ammonia, or amines [J. Med. Chem. 12 (1969) 41, J. Am. Chem. Soc. 82 (1960) 3760]. The 6-substituted 2,4-dichloro-1,3,5-triazines, which are employed as starting compounds for this purpose, can be prepared, for example, from cyanuric chloride and Grignard compounds which are substituted in the 6-position on the triazine ring like the organic radical [Helv. Chim. Acta 33 (1950) 1368]. Alternatively, they can be synthesized from trichloromethyl isocyanide dichloride and amidines which are substituted in the 6-position on the triazine ring like the organic radical (cf. DE-A-1178437).

The disadvantages of the known processes are the limited availability, in particular the lack of availability of the Grignard compounds for the preparation of triazines with alkyl radicals in the 6-position, and frequently poor yields when reacting the dichlorotriazines with ammonia or amines.

It is an object of the invention to prepare in an alternative and preferably advantageous manner 2-amino-4-chloro-1,3,5-triazines which have unsubstituted or substituted aliphatic hydrocarbon radicals in the 6-position. This is also intended to make available some novel triazines of the formula (I).

The invention relates to a process for the preparation of compounds of the formula (I) or salts thereof

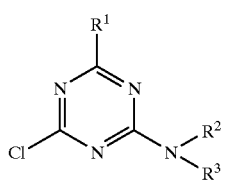
(I)

in which
R$^1$ is (C$_1$–C$_8$)alkyl or (C$_3$–C$_8$)cycloalkyl, where each of the two above radicals independently of the other is unsubstituted or substituted, preferably unsubstituted or substituted by one or more radicals selected from the group consisting of halogen, hydroxyl, cyano, nitro, thiocyanato, formyl, (C$_1$–C$_8$)alkoxy, (C$_1$–C$_8$)alkylthio, (C$^1$–C$_8$)alkylsulfinyl, (C$_1$–C$_8$)alkylsulfonyl, [(C$_1$–C$_8$)-alkyl]carbonyl, [(C$_1$–C$_8$)alkoxy]carbonyl, (C$_2$–C$_8$)alkenyl, (C$_2$–C$_8$)alkynyl, (C$_3$–C$_8$)cycloalkyl, phenyl and, in the case of cycloalkyl, also (C$_1$–C$_8$)alkyl, each of the last-mentioned 11 radicals being unsubstituted or substituted by one or more radicals selected from the group consisting of halogen, (C$_1$–C$_4$)alkoxy, (C$_1$–C$_4$)alkylthio and, in the case of cyclic radicals, also (C$_1$–C$_4$) alkyl and (C$_1$–C$_4$)haloalkyl, and R$^2$, R$^3$ in each case independently of one another are hydrogen, amino, hydroxyl, formyl or unsubstituted or substituted (C$_1$–C$_8$)alkyl, (C$_1$–C$_8$)alkylamino, di[(C$_1$–C$_8$)alkyl]amino, (C$_1$–C$_8$)alkyloxy, aryl, aryloxy, (C$_3$–C$_8$)cycloalkyl, [(C$_1$–C$_8$)alkyl]carbonyl, [(C$_1$–C$_8$)alkoxy]carbonyl, arylcarbonyl, aryloxycarbonyl, (C$_1$–C$_8$)alkylsulfonyl, arylsulfonyl or an unsubstituted or substituted heterocyclyl radical, heterocyclyloxy radical, heterocyclylamino radical, each of which has 3 to 6 ring atoms and 1 to 3 hetero ring atoms selected from the group consisting of N, O and S, or R$^2$, R$^3$ together with the nitrogen atom of the group NR$^2$R$^3$ are a heterocyclic radical having 3 to 6 ring atoms and 1 to 4 hetero ring atoms, where, in addition to the nitrogen atom, the other hetero ring atoms which may exist are selected from the group consisting of N, O and S and the heterocycle is unsubstituted or substituted.

which comprises converting 2-amino-4-thio-1,3,5-triazines of the general formula (II)

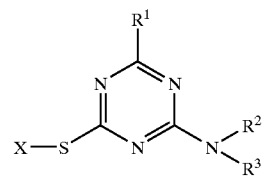
(II)

in which X represents hydrogen, (C$_1$–C$_6$)alkyl, (C$_2$–C$_6$) alkenyl, (C$_2$–C$_6$)alkynyl or phenyl, where each of the last-mentioned 4 radicals is unsubstituted or substituted, or represents a 2-amino-4-thio-1,3,5-triazine radical which is bonded via sulfur and equally substituted by chlorination into the compound (I).

The 2-amino-4-thio-1,3,5-triazines (II), which act as starting materials, are known or can be prepared analogously to known processes [cf. DE-A-4139624, Chem. Ber. 100 (1967) 1874–1891, J. Heterocyclic Chem. 27 (1990) 1565–1568, J. Heterocyclic Chem. 23 (1986) 1709–1714].

A chlorinating agent is required in the process according to the invention, for example chlorine, salts of hypochlorous acid, phosphorus pentachloride, phosphoryl chloride (=phosphorus oxychloride) or thionyl chloride, preferably chlorine.

The chlorinating agent is employed, for example, in amounts of 1 to 100 equivalents based on the compound of the formula (II), preferably 1 to 10 equivalents, in particular in equimolar amounts up to an excess, which allows a reaction of the compound of the formula (II) to take place. An equivalent in this context is to be understood as meaning such an amount of chlorinating agent which is required for reacting the compound (II) according to stoichiometrical reasons.

In principle, the chlorination reaction can be carried out without additional solvent and/or diluent (hereinbelow both: solvent), or, most expediently, in the presence of a solvent. Suitable solvents are preferably organic solvents which are largely inert to the chlorinating agent and the compounds of the formulae (II) and (I) under the reaction conditions. Examples of suitable solvents are:

1. Predominantly aprotic organic solvents which are inert under the reaction conditions, for example aliphatic and aromatic hydrocarbons such as, for example, mineral oils, petroleum ether, cyclohexane or toluene, xylenes, naphthalene derivatives, ®Solvesso 200 (high-boiling aromatic mixture);

halogenated aliphatic and aromatic hydrocarbons such as methylene chloride, dichloroethane, chloroform or chlorobenzene;

cyclic or open-chain ethers such as diethyl ether, di-n-propyl ether, diisopropyl ether, methyl tert-butyl ether, tetrahydrofuran (THF), dioxane, alkylene glycol monoalkyl ethers and alkylene glycol dialkyl ethers such as, for example, propylene glycol monomethyl ether, propylene glycol monoethyl ether, ethylene glycol monomethyl ether or ethylene glycol monoethyl ether, dimethoxyethane, diglyme, triglyme and tetraglyme;

amides such as dimethylformamide (DMF), dimethylacetamide and N-methylpyrrolidone;

ketones such as cyclohexanone, methyl isobutyl ketone (MIBK);

nitriles such as acetonitrile, propionitrile, butyronitrile and benzonitrile;

sulfoxides are sulfones such as dimethyl sulfoxide (DMSO) and sulfolane, carboxylic esters such as the esters of mono-, di- and tricarboxylic acids with aliphatic alcohols having 1 to 10 carbon atoms, for example ethyl formate, methyl acetate, ethyl acetate, n-propyl acetate, i-propyl acetate, esters of acetic acid with n-, i-, sec- or tert-butanol, mixtures of two or more of the abovementioned solvents;

2. Essentially anhydrous, preferably largely anhydrous, protic solvents and their mixtures or mixtures with the abovementioned aprotic solvents. Examples of protic solvents are aliphatic alcohols such as methanol, ethanol, n- or i-propanol, n-, i-, sec- or tert-butanol, glycols;

carboxylic acids, for example those having 1 to 4 carbon atoms such as formic acid, acetic acid, n-propionic acid or n- and isobutanoic acid.

If the compounds of the formula (II) are chlorinated with chlorine, especially suitable solvents are, for example, methylene chloride, chloroform and concentrated acetic acid, preferably the corresponding anhydrous solvents such as, for example, glacial acetic acid.

The reaction can be carried out within a wide temperature range, in some cases depending on the substrate, the chlorinating agent and the solvent, for example at temperatures between −40° C. and the boiling point of the solvent in question, preferably between −20° C. and 100° C., in particular between 0° C. and 50° C. The reaction temperature should be low enough to avoid side reactions, but high enough to allow a conversion within technically feasible reaction times.

As regards the pressure, particular conditions are not required; as a rule, it is possible or expedient to carry out the chlorination reaction under atmospheric pressure.

Generally customary methods may be employed for working up the reaction mixture. After the reaction, it is possible, for example, to pass an inert gas, for example nitrogen gas, through the mixture so as to remove excess chlorine gas, and subsequently to pour the reaction mixture into water. The product is separated from the water and dried. If the chlorination reaction is carried out in the presence of solvents which are miscible with water, such as, for example, carboxylic acids, the reaction mixture is preferably put into an aqueous solution of a base. If the chlorination reaction is carried out in the presence of solvents which are not miscible with water such as, for example, halogenated hydrocarbons, a base which is not soluble in this solvent is preferably added to the reaction mixture after chlorination, and the mixture is filtered and the product separated from the solvent and dried. Suitable bases are customary organic and, preferably, inorganic bases, and aqueous solutions of these, for example hydroxides or carbonates of alkali metals or alkaline earth metals.

Some chlorination reactions of 2-amino-4-alkylthio-1,3,5-triazines are already known, but the triazines are substituted by aromatic radicals in the 6-position on the triazine ring. Thus, chlorination reactions for the preparation of 2,4-dichloro-6-(2-pyridyl)-1,3,5-triazine [Tetrahedron 31 (1975) 1879–1882] or of 2-chloro-4,6-bis(2',4'-dimethylphenyl)-1,3,5-triazine [U.S. Pat. No. 5,084,570] from the corresponding alkylthio-1,3,5-triazines have already been described. The conditions for the chlorination reaction which are given in the known protocols cannot be simply used for the 2-amino-4-thio-1,3,5-triazines of the formula (II) which have unsubstituted or substituted alkyl radicals in the 6-position. In contrast to aromatic radicals in the 6-position, the alkylthio-1,3,5-triazines which have unsubstituted or substituted aliphatic radicals in the 6-position and which are employed in accordance with the invention generally require milder chlorination conditions. Moreover, the amino group in the 2-position can sometimes lead to undesired side reactions and thus to yield losses or lower product purities when using the known chlorination conditions.

With a view to the use of the compounds (I) as intermediates for the synthesis of active substances, the radical $R^1$ preferably has the following meaning:

$R^1$ is $(C_1-C_6)$alkyl which is unsubstituted or substituted by one or more radicals selected from the group consisting of halogen, hydroxyl, cyano, nitro, thiocyanato, formyl, $(C_1-C_4)$alkoxy, $(C_1-C_4)$alkylthio, $(C_1-C_4)$alkylsulfinyl, $(C_1-C_4)$alkylsulfonyl, $[(C_1-C_4)$alkyl]carbonyl, $[(C_1-C_4)$alkoxy]carbonyl, $(C_2-C_4)$alkenyl, $(C_2-C_4)$alkynyl, $(C_3-C_6)$cycloalkyl, phenyl, where each of the last-mentioned 10 radicals is unsubstituted or substituted by one or more radicals selected from the group consisting of halogen, $(C_1-C_4)$alkoxy, $(C_1-C_4)$alkylthio and, in the case of cyclic radicals, also $(C_1-C_4)$alkyl and $(C_1-C_4)$haloalkyl.

$R^1$ is preferably also $(C_3-C_6)$cycloalkyl which is unsubstituted or substituted by one or more radicals selected from the group consisting of halogen, hydroxyl, cyano, nitro, thiocyanato, formyl, $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, $[(C_1-C_4)$alkyl]carbonyl, $[(C_1-C_4)$alkoxy]carbonyl, $(C_2-C_4)$alkenyl, $(C_2-C_4)$alkynyl, $(C_3-C_6)$cycloalkyl, phenyl, where each of the last-mentioned 11 radicals is unsubstituted or substituted by one or more radicals selected from the group consisting of halogen, $(C_1-C_4)$alkoxy, $(C_1-C_4)$alkylthio and, in the case of cyclic radicals, also $(C_1-C_4)$alkyl and $(C_1-C_4)$haloalkyl.

$R^1$ is especially preferably $(C_1-C_6)$alkyl which is unsubstituted or substituted by one or more radicals selected from the group consisting of halogen, preferably fluorine, chlorine or bromine, hydroxyl, methoxy, ethoxy and cyclopropyl.

$R^1$ is especially preferably also $(C_3-C_6)$cycloalkyl which is unsubstituted or substituted by one or more radicals selected from the group consisting of halogen, preferably fluorine, chlorine or bromine, hydroxyl, $(C_1-C_4)$alkoxy, preferably methoxy and ethoxy, $(C_1-C_4)$alkyl, preferably methyl and ethyl, and $(C_1-C_4)$haloalkyl, preferably $CF_3$.

$R^2$, $R^3$ are preferably in each case independently of one another hydrogen, amino, $(C_1-C_6)$alkyl, $(C_1-C_4)$alkylamino, di[$(C_1-C_4)$alkyl]amino, $(C_1-C_4)$alkyloxy, $(C_3-C_6)$cycloalkyl, $(C_1-C_4)$alkyl]carbonyl, [$(C_1-C_4)$alkoxy]carbonyl, phenylcarbonyl, phenoxycarbonyl, $(C_1-C_4)$alkylsulfonyl, phenylsulfonyl or a heterocyclyl radical having 3 to 6 ring atoms and 1 to 3 hetero ring atoms selected from the group consisting of N, O and S, where phenyl in the abovementioned radicals or the heterocyclyl radical independently of one another are unsubstituted or substituted by one or more radicals selected from the group consisting of halogen, preferably fluorine, chlorine or bromine, hydroxyl, $(C_1-C_4)$alkoxy, preferably methoxy and ethoxy, $(C_1-C_4)$alkyl, preferably methyl and ethyl, and $(C_1-C_4)$haloalkyl, preferably $CF_3$, or $R^2$, $R^3$ together with the nitrogen atom of the group $NR^2R^3$ is a heterocyclic radical which has 3 to 6 ring atoms and 1 to 3 hetero ring atoms, where, in addition to the nitrogen atom, the other hetero ring atoms which may be present are selected from the group consisting of N, O and S and the heterocycle is unsubstituted or substituted by one or more radicals selected from the group consisting of halogen, preferably fluorine, chlorine or bromine, hydroxyl, $(C_1-C_4)$alkoxy, preferably methoxy and ethoxy, $(C_1-C_4)$alkyl, preferably methyl and ethyl, and $(C_1-C_4)$haloalkyl, preferably $CF_3$.

The radicals $R^2$, $R^3$ in each case independently of one another are preferably hydrogen, amino, methyl, ethyl, acetyl.

The compounds of the formula (I) can form salts when a basic group such as, for example, amino or alkylamino, undergoes an addition reaction with a suitable inorganic or organic acid such as, for example, HCl, HBr, $H_2SO_4$ or $HNO_3$, but also oxalic acid or sulfonic acids.

With a view to the use of the compounds (II) as intermediates for the synthesis of active substances, the radical X has, for example, the following meaning:

X is, for example, hydrogen, $(C_1-C_6)$alkyl, $(C_2-C_6)$alkenyl or $(C_2-C_6)$alkynyl, where each of the last-mentioned 3 radicals is unsubstituted or substituted by one or more radicals selected from the group consisting of halogen, $(C_1-C_4)$alkoxy, $(C_1-C_4)$alkylthio, $(C_1-C_4)$alkylsulfinyl, $(C_1-C_4)$alkylsulfonyl, [$(C_1-C_4)$alkyl]carbonyl, [$(C_1-C_4)$alkoxy]carbonyl, $(C_3-C_6)$cycloalkyl and phenyl, each of the last-mentioned 10 radicals being unsubstituted or substituted by one or more radicals selected from the group consisting of halogen, $(C_1-C_4)$alkoxy, $(C_1-C_4)$alkylthio and, in the case of cyclic radicals, also $(C_1-C_4)$alkyl and $(C_1-C_4)$haloalkyl or represents phenyl which is unsubstituted or substituted by one or more radicals selected from the group consisting of halogen, cyano, nitro, $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, [$(C_1-C_4)$alkyl]carbonyl, [$(C_1-C_4)$alkoxy]carbonyl, $(C_2-C_4)$alkenyl, $(C_2-C_4)$alkynyl, $(C_3-C_6)$cycloalkyl, each of the last-mentioned 10 radicals being unsubstituted or substituted by one or more radicals selected from the group consisting of halogen, $(C_1-C_4)$alkoxy, $(C_1-C_4)$alkylthio and, in the case of cyclic radicals, also $(C_1-C_4)$alkyl and $(C_1-C_4)$haloalkyl, or represents a 2-amino-4-thio-1,3,5-triazine radical which is bonded via sulfur and equally substituted, X preferably represents $(C_1-C_4)$alkyl which is unsubstituted or substituted by one or more radicals selected from the group consisting of halogen, $(C_1-C_4)$alkoxy, $(C_1-C_4)$alkylthio, $(C_3-C_6)$cycloalkyl and phenyl, each of the last-mentioned 4 radicals being unsubstituted or substituted by one or more radicals selected from the group consisting of halogen, $(C_1-C_4)$alkoxy, $(C_1-C_4)$alkylthio and, in the case of cyclic radicals, also $(C_1-C_4)$alkyl and $(C_1-C_4)$haloalkyl, or represents phenyl which is unsubstituted or substituted by one or more radicals selected from the group consisting of halogen, cyano, nitro, $(C_1-C_4)$alkyl, $(C_1-C_4)$haloalkyl, $(C_1-C_4)$alkoxy, $(C_1-C_4)$haloalkoxy, $(C_1-C_4)$alkylthio and [$(C_1-C_4)$alkoxy]carbonyl, or represents a 2-amino-4-thio-1,3,5-triazine radical which is bonded via sulfur and equally substituted, X represents, in particular, $(C_1-C_4)$alkyl, benzyl or phenyl, where each of the last-mentioned two groups is unsubstituted in the phenyl moiety or substituted by one or more radicals selected from the group consisting of halogen, cyano, nitro, $(C_1-C_4)$alkyl, preferably methyl, $(C_1-C_4)$haloalkyl, preferably $CF_3$ or $CCl_3$, $(C_1-C_4)$alkoxy, preferably methoxy, $(C_1-C_4)$haloalkoxy, preferably $OCHF_2$, and $(C_1-C_4)$alkylthio.

In the abovementioned formulae, the radicals alkyl, alkoxy, haloalkyl, haloalkoxy, alkylamino and alkylthio and the corresponding unsaturated and/or substituted radicals in the carbon skeleton can in each case be straight-chain or branched. Unless otherwise specified, the lower carbon skeletons, for example those having 1 to 6 carbon atoms, or in the case of unsaturated groups, 2 to 6 carbon atoms, are preferred for these radicals. Alkyl radicals, also in the composite meanings such as alkoxy, haloalkyl and the like, are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals have the meanings of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Cycloalkyl is a carbocyclic saturated ring system having preferably 3–8 carbon atoms, for example cyclopropyl, cyclobutyl, cyclopentyl or cyclohexyl.

Halogen is, for example, fluorine, chlorine, bromine or iodine. Haloalkyl, -alkenyl and -alkynyl are alkyl, alkenyl or alkynyl which are partially or fully substituted by halogen, preferably by fluorine, chlorine and/or bromine, in particular by fluorine and/or chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this also applies analogously to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and and the like, preferably phenyl.

A heterocyclic radical or ring (heterocyclyl) can be saturated, unsaturated or heteroaromatic; it preferably contains one or more, in particular 1, 2 or 3, hetero atoms in the heterocyclic ring, preferably selected from the group consisting of N, O and S; it is preferably an aliphatic heterocyclyl radical having 3 to 7 ring atoms or a heteroaromatic radical having 5 or 6 ring atoms. The heterocyclic radical can be, for example, a heteroaromatic radical or ring (heteroaryl) such as, for example, a mono-, bi- or polycyclic aromatic system in which at least 1 ring contains one or more hetero atoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl and imidazolyl, or is partially or fully hydrogenated radical such as oxiranyl, pyrrolidyl, piperidyl, piperazinyl, dioxolanyl, oxazolinyl, isoxazolinyl, oxazolidinyl, isoxazolidinyl, morpholinyl, tetrahydrofuryl. Substituents which are suitable for a substituted heterocyclic radical are the substituents mentioned further below, and additionally also oxo. The oxo group may also occur on the hetero ring atoms, which may exist in various degrees of oxidation, for example in the case of N and S.

Substituted radicals such as a substituted alkyl, alkenyl, alkynyl, aryl, phenyl, benzyl, heterocyclyl and heteroaryl radical, are, for example, a substituted radical derived from the unsubstituted parent structure, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl; the term "substituted radicals" such as substituted alkyl and the like includes, as substituents, in addition to the abovementioned saturated hydrocarbon-containing radicals the corresponding unsaturated aliphatic and aromatic radicals, such as unsubstituted or substituted alkenyl, alkynyl, alkenyloxy, alkynyloxy, phenyl, phenoxy and the like. In the case of radicals having carbon atoms, those having 1 to 4 carbon atoms, in particular 1 or 2 carbon atoms, are preferred. Preferred are, as a rule, substituents selected from the group consisting of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Especially preferred in this context are the substituents methyl, methoxy and chlorine.

The formula (I) and (II) also encompass all stereoisomers. Such compounds contain one or more asymmetric carbon atoms or else double bonds which are not mentioned specifically in the formulae. The stereoisomers which are possible and which are defined by their specific spatial form, such as enantiomers, diastereomers, Z- and E-isomers, can be obtained by customary methods from mixtures of the stereoisomers or else be prepared by stereoselective reactions in combination with the use of stereochemically pure starting materials.

It is preferred to react the compounds (I) with amines of the formula (III)

A—NH—R (III), with exchange of the chlorine atom, to give herbicidal aminotriazines of the formula (IV)

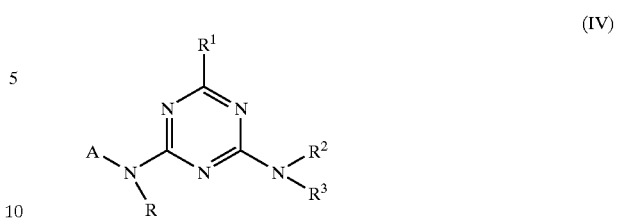

where, in formulae (III) and (IV), the radicals $R^1$, $R^2$, $R^3$ are as defined in formula (I) and A and R are radicals which in conjunction with the remaining molecular structure of the formula (IV) constitute the chemical structure of a herbicidally active aminotriazine.

The herbicidal aminotriazines are preferably those from the publications WO-A-90/09378, WO-A-96/25404, WO-A-97/00254, WO-A-97/08156, WO-A-97/19936, WO-A-97/29095, WO-A-97/31904, WO-A-97/35481, WO-A-98/10654, WO-A-98/15536, WO-A-98/15537, WO-A-98/15538, WO-A-98/15539, the International Application No. PCT/EP98/00283 and the German Patent Application No. 19826670.7, which have already been mentioned at the outset, but the radicals $R^1$, $R^2$ and $R^3$ are as defined in the abovementioned process according to the invention. The definition of the herbicidal aminotriazines from the publications is specifically incorporated by reference; they are thus part of the present description.

In formula (IV), the radical A is preferably a $(C_1-C_6)$ alkylene chain which is substituted in the α-position relative to the amino group by an unsubstituted or substituted alkyl radical and in the ω-position by an unsubstituted or substituted aryl, heteroaryl, aryloxy or heteroaryloxy radical and which can also have further substituents selected from the group consisting of halogen, alkyl, alkoxy and hydroxyl.

R is preferably H or alkyl such as $(C_1-C_4)$alkyl, in particular H.

Especially preferred are the preferred herbicidal aminotriazines which are mentioned in the above publications, in particular the compounds which are in each case defined specifically, such as the preparation examples and the individually defined tabulated examples, as long as the radicals which correspond to the radicals $R^1$, $R^2$ and $R^3$ in formula (IV) are defined within the scope of the present invention.

The invention therefore also relates to a process for the preparation of herbicidal aminotriazines of the formula (IV), which comprises first preparing, in accordance with the invention, a compound of the formula (I) and then reacting it with an amine of the formula (III) to give the compound of the formula (IV).

Reaction conditions for reacting the compounds of the formulae (I) and (III) are known in principle from the publications mentioned in connection with the herbicidal aminotriazines (IV) and from the literature cited therein, or can be carried out analogously to the standard reactions known to the skilled worker for reacting heteroaromatic chlorine compounds with amines.

The invention generally also relates to the use of compounds of the formula (I) or salts thereof which have been obtained by the process according to the invention for the preparation of the compounds (I) for the preparation of bioactive substances from the chemical class of the aminotriazines, preferably the herbicidal aminotriazines.

In the examples which follow, quantities are by weight unless otherwise specified. Conventional abbreviations are used for units and physical quantities, for example h=hour(s), m.p.=melting point, l=liter, g=gram, min=minute(s), in vacuo=under reduced pressure

EXAMPLES a) 2-Amino-4-methylthio-6-(1-fluoroisopropyl)-1,3,5-triazine 125 g of 2-fluoroisobutyroyl chloride and 300 ml of triethylamine were simultaneously added dropwise (0.5 h) at approx. 20° C. to a solution of 245 g of S-methylguanyl-isothiourea methylsulfate and 250 g of sodium sulfate in 1 liter of anhydrous N-methylpyrrolidone. After the reaction mixture had been stirred for 3 h at 50° C., the cooled mixture was poured into 5 liters of water. The crude product which has precipitated is filtered off with suction and extracted by stirring with heptane. After filtration with suction and drying, 150 g (75%) of 2-amino-4-methylthio-6-(1-fluoroisopropyl)-1,3,5-triazine were obtained as a white powder (m.p. 155° C.).

$^1$H NMR (CDCl$_3$): δ=1.7 (d, 6H), 2.5 (s, 3H), 5.7 (s br., 1H), 6.9 (s br., 1H).

b) 2-Amino-4-chloro-6-(1-fluoroisopropyl)-1,3,5-triazine (Table 1, Example 25)

Chlorine gas was passed at 20 to 25° C. into a suspension of 150 g of 2-amino-4-methylthio-6-(1-fluoroisopropyl)-1,3,5-triazine in 1 liter of glacial acetic acid (15 min). The reaction mixture was stirred for 30 min at approx. 20° C., flushed with nitrogen gas for 1 h at room temperature, poured into 5 liters of ice-cold aqueous solution of 350 g of sodium hydroxide and stirred for 5 min. After filtration with suction and drying, 110 g (80%) of 2-amino-4-chloro-6-(1-fluoroisopropyl)-1,3,5-triazine were obtained as a white powder (m.p. 185° C.).

$^1$H NMR (CDCl$_3$): δ=1.7 (d, 6H), 6.2 (s br., 1H), 6.9 (s br., 1H).

c) 2-Amino-4-chloro-6-(1-fluoroethyl)-1,3,5-triazine (Table 1, Example 21)

Chlorine gas was passed into a suspension of 38 g of 2-amino-4-methylthio-6-(1-fluoroethyl)-1,3,5-triazine in 0.25 l of glacial acetic acid (15 min) at 20 to 25° C. The reaction mixture was stirred for 30 min at approx. 20° C., sprayed for 1 hour with nitrogen gas at room temperature, poured into 1.25 l of ice-cold aqueous solution of 87 g of sodium hydroxide and stirred for 5 min. After extraction with ethyl acetate, the organic phase was washed with water and dried over magnesium sulfate, and the solvent was removed in vacuo. The crude product was purified by stirring in heptane. After filtration with suction and drying, 25 g (70%) of 2-amino-4-chloro-6-(1-fluoroethyl)-1,3,5-triazine were obtained as a white powder (m.p. 131° C.); $^1$H NMR (CDCl$_3$): δ=1.7 (dd, 3 H), 5.4 (dq, 1 H), 6.1 (s br., 1 H), 6.7 (s br., 1H).

d) 2-Amino-4-chloro-6-trifluoromethyl-1,3,5-triazine (Table 1, Example 15)

Chlorine gas was passed into a solution of 21 g of 2-amino-4-methylthio-6-trifluoromethyl-1,3,5-triazine in 0.2 l glacial acetic acid at 20 to 25° C. (15 min). The reaction mixture was stirred for 30 min at approx. 20° C., sprayed for 1 hour with nitrogen gas at room temperature, poured into 1 l of ice-cold aqueous solution of 70 g of sodium hydroxide and stirred for 5 min. After extraction with ethyl acetate, the organic phase was washed with water and dried over magnesium sulfate, and the solvent was removed in vacuo. The crude product was purified by stirring in heptane. After filtration with suction and drying, 12 g (60%) of 2-amino-4-chloro-6-trifluoromethyl-1,3,5-triazine were obtained as a white powder (m.p. 109° C.); $^1$H NMR (CDCl$_3$): δ=6.4 (s br., 2H).

e) 2-Amino-4-chloro-6-(1-chloroisopropyl)-1,3,5-triazine (Table 1, Example 32)

Chlorine gas was passed at 20 to 25° C. into a suspension of 110 g of 2-amino-4-methylthio-6-(1-chloroisopropyl)-1,3,5-triazine in 0.75 l of glacial acetic acid (30 min). The reaction mixture was stirred for 30 min at approx. 20° C., sprayed with nitrogen gas for 1 h at room temperature, poured into 3.75 l of ice-cold aqueous solution of 260 g of sodium hydroxide and stirred for 5 min. After filtration with suction and drying, 83 g (80%) of 2-amino-4-chloro-6-(1-chloroisopropyl)-1,3,5-triazine were obtained as a white powder (m.p. 110° C.); $^1$H NMR (CDCl$_3$): δ=1.9 (s, 6 H), 6.0 (s br., 2 H).

f) Comparative example anologous to the chlorination described in U.S. Pat. No. 5,084,570 [conditions for (het) aryl-substituted 2-amino-4-alkylthio-1,3,5-triazines]

Chlorine gas was passed at 35 to 40° C. into a solution of 5 g of 2-amino-4-methylthio-6-(1-chloroisopropyl)-1,3,5-triazine in 0.1 l of trichloromethane (or tetrachloromethane) (15 min). 10 g of potassium carbonate were added to the reaction mixture at room temperature, and the mixture was stirred for 5 minutes and filtered and the solvent removed in vacuo. This gave a product mixture in which approximately 0.5 g (10%) of 2-amino-4-chloro-6-(1-chloroisopropyl)-1,3,5-triazine are present (detection by HPLC comparison with 100% product).

The table which follows shows the abovementioned examples according to the invention in addition to other examples obtained analogously. The chlorination products of the formula (I) are obtained, as a rule, in yields of 60 to 95% of theory.

The following abbreviations are used in Table 1 which follows:

Me=methyl c-Pr=cyclopropyl c-Bu=cyclobutyl; n-Bu=n-butyl c-Pe=cyclopentyl

Ac=acetyl

TABLE 1

Compounds of the formula (I)

(I)

| No. | R$^1$ | R$^2$ | R$^3$ |
|---|---|---|---|
| 1 | CH$_3$ | H | H |
| 2 | C$_2$H$_5$ | H | H |
| 3 | C$_3$H$_7$ | H | H |
| 4 | CH(CH$_3$)$_2$ | H | H |
| 5 | c-Pr | H | H |
| 6 | n-C$_4$H$_9$ | H | H |
| 7 | CH(CH$_3$)C$_2$H$_5$ | H | H |
| 8 | c-Bu | H | H |
| 9 | n-C$_5$H$_{11}$ | H | H |
| 10 | c-Pe | H | H |
| 11 | CH$_2$-c-Pr | H | H |

TABLE 1-continued

Compounds of the formula (I)

| No. | R¹ | R² | R³ |
|---|---|---|---|
| 12 | -C(CH₃)(CH₂CH₂) (1-methylcyclopropyl) | H | H |
| 13 | CH₂F | H | H |
| 14 | CHF₂ | H | H |
| 15 | CF₃ | H | H |
| 16 | CH₂Cl | H | H |
| 17 | CHCl₂ | H | H |
| 18 | CCl₃ | H | H |
| 19 | CClF₂ | H | H |
| 20 | CFCl₂ | H | H |
| 21 | CHFCH₃ | H | H |
| 22 | CF₂CH₃ | H | H |
| 23 | CF₂CF₂H | H | H |
| 24 | CF₂CF₃ | H | H |
| 25 | CF(CH₃)₂ | H | H |
| 26 | CH(CF₃)CH₃ | H | H |
| 27 | CF(CF₃)CH₃ | H | H |
| 28 | CH(CF₃)₂ | H | H |
| 29 | CF(CF₃)₂ | H | H |
| 30 | CHClCH₃ | H | H |
| 31 | CCl₂CH₃ | H | H |
| 32 | CCl(CH₃)₂ | H | H |
| 33 | CFCl—CH₃ | H | H |
| 34 | -C(F)(CH₂CH₂) (1-fluorocyclopropyl) | H | H |
| 35 | -C(Cl)(CH₂CH₂) (1-chlorocyclopropyl) | H | H |
| 36 | CH₂OCH₃ | H | H |
| 37 | CH(CH₃)OCH₃ | H | H |
| 38 | C(CH₃)₂OCH₃ | H | H |
| 39 | C₂H₅OCH₃ | H | H |
| 40 | CH(CH₃)CH₂OCH₃ | H | H |
| 41 | -C(OMe)(CH₂CH₂) (1-methoxycyclopropyl) | H | H |
| 42 | CH₂OH | H | H |
| 43 | CH(CH₃)OH | H | H |
| 44 | C(CH₃)₂OH | H | H |
| 45 | C₂H₅OH | H | H |
| 46 | CH(CH₃)CH₂OH | H | H |
| 47 | -C(OH)(CH₂CH₂) (1-hydroxycyclopropyl) | H | H |
| 48 | CH₃ | Me | H |
| 49 | C₂H₅ | Me | H |
| 50 | C₃H₇ | Me | H |
| 51 | CH(CH₃)₂ | Me | H |
| 52 | c-Pr | Me | H |
| 53 | n-C₄H₉ | Me | H |
| 54 | CH(CH₃)C₂H₅ | Me | H |
| 55 | c-Bu | Me | H |
| 56 | n-C₅H₁₁ | Me | H |
| 57 | c-Pe | Me | H |
| 58 | CH₂-c-Pr | Me | H |
| 59 | -C(CH₃)(CH₂CH₂) (1-methylcyclopropyl) | Me | H |
| 60 | CH₂F | Me | H |
| 61 | CHF₂ | Me | H |
| 62 | CF₃ | Me | H |
| 63 | CH₂Cl | Me | H |
| 64 | CHCl₂ | Me | H |
| 65 | CCl₃ | Me | H |
| 66 | CClF₂ | Me | H |
| 67 | CFCl₂ | Me | H |
| 68 | CHFCH₃ | Me | H |
| 69 | CF₂CH₃ | Me | H |
| 70 | CF₂CF₂H | Me | H |
| 71 | CF₂CF₃ | Me | H |
| 72 | CF(CH₃)₂ | Me | H |
| 73 | CH(CF₃)CH₃ | Me | H |
| 74 | CF(CF₃)CH₃ | Me | H |
| 75 | CH(CF₃)₂ | Me | H |
| 76 | CF(CF₃)₂ | Me | H |
| 77 | CHClCH₃ | Me | H |
| 78 | CCl₂CH₃ | Me | H |
| 79 | CCl(CH₃)₂ | Me | H |
| 80 | CFCl—CH₃ | Me | H |
| 81 | -C(F)(CH₂CH₂) (1-fluorocyclopropyl) | Me | H |
| 82 |  | Me | H |
| 83 | CH₂OCH₃ | Me | H |
| 84 | CH(CH₃)OCH₃ | Me | H |
| 85 | C(CH₃)₂OCH₃ | Me | H |
| 86 | C₂H₅OCH₃ | Me | H |
| 87 | CH(CH₃)CH₂OCH₃ | Me | H |
| 88 | -C(OMe)(CH₂CH₂) (1-methoxycyclopropyl) | Me | H |
| 89 | CH₂OH | Me | H |
| 90 | CH(CH₃)OH | Me | H |
| 91 | C(CH₃)₂OH | Me | H |
| 92 | C₂H₅OH | Me | H |
| 93 | CH(CH₃)CH₂OH | Me | H |
| 94 | -C(OH)(CH₂CH₂) (1-hydroxycyclopropyl) | Me | H |
| 95 | CH₃ | Me | Me |
| 96 | C₂H₅ | Me | Me |
| 97 | C₃H₇ | Me | Me |
| 98 | CH(CH₃)₂ | Me | Me |
| 99 | c-Pr | Me | Me |
| 100 | n-C₄H₉ | Me | Me |
| 101 | CH(CH₃)C₂H₅ | Me | Me |

TABLE 1-continued

Compounds of the formula (I)

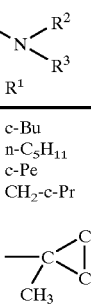

| No. | R¹ | R² | R³ |
|---|---|---|---|
| 102 | c-Bu | Me | Me |
| 103 | n-C₅H₁₁ | Me | Me |
| 104 | c-Pe | Me | Me |
| 105 | CH₂-c-Pr | Me | Me |
| 106 |  | Me | Me |
| 107 | CH₂F | Me | Me |
| 108 | CHF₂ | Me | Me |
| 109 | CF₃ | Me | Me |
| 110 | CH₂Cl | Me | Me |
| 111 | CHCl₂ | Me | Me |
| 112 | CCl₃ | Me | Me |
| 113 | CClF₂ | Me | Me |
| 114 | CFCl₂ | Me | Me |
| 115 | CHFCH₃ | Me | Me |
| 116 | CF₂CH₃ | Me | Me |
| 117 | CF₂CF₂H | Me | Me |
| 118 | CF₂CF₃ | Me | Me |
| 119 | CF(CH₃)₂ | Me | Me |
| 120 | CH(CF₃)CH₃ | Me | Me |
| 121 | CF(CF₃)CH₃ | Me | Me |
| 122 | CH(CF₃)₂ | Me | Me |
| 123 | CF(CF₃)₂ | Me | Me |
| 124 | CHClCH₃ | Me | Me |
| 125 | CCl₂CH₃ | Me | Me |
| 126 | CCl(CH₃)₂ | Me | Me |
| 127 | CFCl—CH₃ | Me | Me |
| 128 |  | Me | Me |
| 129 |  | Me | Me |
| 130 | CH₂OCH₃ | Me | Me |
| 131 | CH(CH₃)OCH₃ | Me | Me |
| 132 | C(CH₃)₂OCH₃ | Me | Me |
| 133 | C₂H₅OCH₃ | Me | Me |
| 134 | CH(CH₃)CH₂OCH₃ | Me | Me |
| 135 |  | Me | Me |
| 136 | CH₂OH | Me | Me |
| 137 | CH(CH₃)OH | Me | Me |
| 138 | C(CH₃)₂OH | Me | Me |
| 139 | C₂H₅OH | Me | Me |
| 140 | CH(CH₃)CH₂OH | Me | Me |
| 141 | 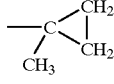 | Me | Me |
| 142 | CH₃ | Ac | H |
| 143 | C₂H₅ | Ac | H |
| 144 | C₃H₇ | Ac | H |
| 145 | CH(CH₃)₂ | Ac | H |
| 146 | c-Pr | Ac | H |
| 147 | n-C₄H₉ | Ac | H |
| 148 | CH(CH₃)C₂H₅ | Ac | H |
| 149 | c-Bu | Ac | H |
| 150 | n-C₅H₁₁ | Ac | H |
| 151 | c-Pe | Ac | H |
| 152 | CH₂-c-Pr | Ac | H |
| 153 | 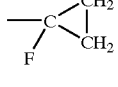 | Ac | H |
| 154 | CH₂F | Ac | H |
| 155 | CHF₂ | Ac | H |
| 156 | CF₃ | Ac | H |
| 157 | CH₂Cl | Ac | H |
| 158 | CHCl₂ | Ac | H |
| 159 | CCl₃ | Ac | H |
| 160 | CClF₂ | Ac | H |
| 161 | CFCl₂ | Ac | H |
| 162 | CHFCH₃ | Ac | H |
| 163 | CF₂CH₃ | Ac | H |
| 164 | CF₂CF₂H | Ac | H |
| 165 | CF₂CF₃ | Ac | H |
| 166 | CF(CH₃)₂ | Ac | H |
| 167 | CH(CF₃)CH₃ | Ac | H |
| 168 | CF(CF₃)CH₃ | Ac | H |
| 169 | CH(CF₃)₂ | Ac | H |
| 170 | CF(CF₃)₂ | Ac | H |
| 171 | CHClCH₃ | Ac | H |
| 172 | CCl₂CH₃ | Ac | H |
| 173 | CCl(CH₃)₂ | Ac | H |
| 174 | CFCl—CH₃ | Ac | H |
| 175 | 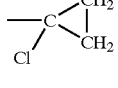 | Ac | H |
| 176 | 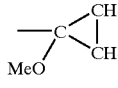 | Ac | H |
| 177 | CH₂OCH₃ | Ac | H |
| 178 | CH(CH₃)OCH₃ | Ac | H |
| 179 | C(CH₃)₂OCH₃ | Ac | H |
| 180 | C₂H₅OCH₃ | Ac | H |
| 181 | CH(CH₃)CH₂OCH₃ | Ac | H |
| 182 |  | Ac | H |
| 183 | CH₂OH | Ac | H |
| 184 | CH(CH₃)OH | Ac | H |
| 185 | C(CH₃)₂OH | Ac | H |
| 186 | C₂H₅OH | Ac | H |
| 187 | CH(CH₃)CH₂OH | Ac | H |

TABLE 1-continued

Compounds of the formula (I)

(I)

Structure: triazine with R¹ at top, Cl at left, and N(R²)(R³) at right

| No. | R¹ | R² | R³ |
|---|---|---|---|
| 188 | -C(CH₂)(CH₂)OH (hydroxymethyl-cyclopropyl) | Ac | H |
| 189 | CH₃ | NH₂ | H |
| 190 | C₂H₅ | NH₂ | H |
| 191 | C₃H₇ | NH₂ | H |
| 192 | CH(CH₃)₂ | NH₂ | H |
| 193 | c-Pr | NH₂ | H |
| 194 | n-C₄H₉ | NH₂ | H |
| 195 | CH(CH₃)C₂H₅ | NH₂ | H |
| 196 | c-Bu | NH₂ | H |
| 197 | n-C₅H₁₁ | NH₂ | H |
| 198 | c-Pe | NH₂ | H |
| 199 | CH₂-c-Pr | NH₂ | H |
| 200 | -C(CH₃)(CH₂)(CH₂) (methyl-cyclopropyl) | NH₂ | H |
| 201 | CH₂F | NH₂ | H |
| 202 | CHF₂ | NH₂ | H |
| 203 | CF₃ | NH₂ | H |
| 204 | CH₂Cl | NH₂ | H |
| 205 | CHCl₂ | NH₂ | H |
| 206 | CCl₃ | NH₂ | H |
| 207 | CClF₂ | NH₂ | H |
| 208 | CFCl₂ | NH₂ | H |
| 209 | CHFCH₃ | NH₂ | H |
| 210 | CF₂CH₃ | NH₂ | H |
| 211 | CF₂CF₂H | NH₂ | H |
| 212 | CF₂CF₃ | NH₂ | H |
| 213 | CF(CH₃)₂ | NH₂ | H |
| 214 | CH(CF₃)CH₃ | NH₂ | H |
| 215 | CF(CF₃)CH₃ | NH₂ | H |
| 216 | CH(CF₃)₂ | NH₂ | H |
| 217 | CF(CF₃)₂ | NH₂ | H |
| 218 | CHClCH₃ | NH₂ | H |
| 219 | CCl₂CH₃ | NH₂ | H |
| 220 | CCl(CH₃)₂ | NH₂ | H |
| 221 | CFCl—CH₃ | NH₂ | H |
| 222 | -C(F)(CH₂)(CH₂) (fluoro-cyclopropyl) | NH₂ | H |
| 223 | -C(Cl)(CH₂)(CH₂) (chloro-cyclopropyl) | NH₂ | H |
| 224 | CH₂OCH₃ | NH₂ | H |
| 225 | CH(CH₃)OCH₃ | NH₂ | H |
| 226 | C(CH₃)₂OCH₃ | NH₂ | H |
| 227 | C₂H₅OCH₃ | NH₂ | H |
| 228 | CH(CH₃)CH₂OCH₃ | NH₂ | H |
| 229 | -C(OMe)(CH₂)(CH₂) (methoxy-cyclopropyl) | NH₂ | H |
| 230 | CH₂OH | NH₂ | H |
| 231 | CH(CH₃)OH | NH₂ | H |
| 232 | C(CH₃)₂OH | NH₂ | H |
| 233 | C₂H₅OH | NH₂ | H |
| 234 | CH(CH₃)CH₂OH | NH₂ | H |
| 235 | -C(OH)(CH₂)(CH₂) (hydroxy-cyclopropyl) | NH₂ | H |

What is claimed is:

1. A process for the preparation of compounds of the formula (I) or salts thereof (I)

in which $R^1$ is $(C_1-C_8)$alkyl or $(C_3-C_8)$cycloalkyl, which is independently of one another unsubstituted or substituted by one or more radicals selected from the group consisting of halogen, hydroxyl, cyano, nitro, thiocyanato, formyl, $(C_1-C_8)$alkoxy, $(C_1-C_8)$alkylthio, $(C_1-C_8)$alkylsulfinyl, $(C_1-C_8)$alkylsulfonyl, $[(C_1-C_8)$-alkyl]carbonyl, $[(C_1-C_8)$alkoxy]carbonyl, $(C_3-C_8)$cycloalkyl, phenyl and, in the case of cycloalkyl, also $(C_1-C_8)$alkyl, each of the last-mentioned 9 radicals being unsubstituted or substituted by one or more radicals selected from the group consisting of halogen, $(C_1-C_4)$alkoxy, $(C_1-C_4)$alkylthio and, in the case of cyclic radicals, also $(C_1-C_4)$alkyl and $(C_1-C_4)$haloalkyl, and $R^2, R^3$ in each case independently of one another are hydrogen, amino, $(C_1-C_6)$alkyl, $(C_1-C_4)$alkylamino, di[$(C_1-C_4)$alkyl]amino, $(C_1-C_4)$alkyloxy, $(C_3-C_6)$cycloalkyl, $[(C_1-C_4)$alkyl]carbonyl, $[(C_1-C_4)$alkoxy]carbonyl, phenylcarbonyl, phenoxycarbonyl, $(C_1-C_4)$alkylsulfonyl, phenylsulfonyl or a saturated heterocyclyl radical having 3 to 6 ring atoms and 1 to 3 hetero ring atoms selected from the group consisting of N, O and S, where phenyl in the abovementioned radicals or the heterocyclyl radical independently of one another are unsubstituted or substituted by one or more radicals selected from the group consisting of halogen, hydroxyl, $(C_1-C_4)$alkoxy, $(C_1-C_4)$alkyl, and $(C_1-C_4)$haloalkyl, or $R^2, R^3$ together with the nitrogen atom of the group $NR^2R^3$ is a saturated heterocyclic radical which has 3 to 6 ring atoms and 1 to 3 hetero ring atoms, where, in addition to the nitrogen atom, the other hetero ring atoms which may be present are selected from the group consisting of N, O and S and the heterocycle is unsubstituted or substituted by one or more radicals selected from the group consisting of halogen, hydroxyl, ($C_1$–$C_4$)alkoxy, ($C_1$–$C_4$)alkyl and ($C_1$–$C_4$)haloalkyl, which comprises converting 2-amino-4-thio-1,3,5-triazines of the formula (II)

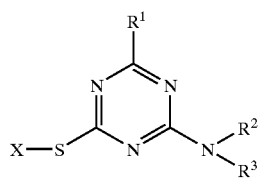

(II)

in which X represents ($C_1$–$C_4$)alkyl which is unsubstituted or substituted by one or more radicals selected from the group consisting of halogen, ($C_1$–$C_4$)alkoxy, ($C_1$–$C_4$)alkylthio, ($C_3$–$C_6$)cycloalkyl and phenyl, each of the last-mentioned 4 radicals being unsubstituted or substituted by one or more radicals selected from the group consisting of halogen, ($C_1$–$C_4$)alkoxy, ($C_1$–$C_4$)alkylthio and, in the case of cyclic radicals, also ($C_1$–$C_4$)alkyl and ($C_1$–$C_4$)haloalkyl, or represents phenyl which is unsubstituted or substituted by one or more radicals selected from the group consisting of halogen, cyano, nitro, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio and [($C_1$–$C_4$)alkoxy]carbonyl, or represents a 2-amino-4-thio-1,3,5-triazine radical which is bonded via sulfur and equally substituted, by chlorination in the presence of an essentially anhydrous protic solvent.

2. The process as claimed in claim 1, wherein
$R^1$ is ($C_1$–$C_6$)alkyl which is unsubstituted or substituted by one or more radicals selected from the group consisting of halogen, hydroxyl, cyano, nitro, thiocyanato, formyl, ($C_1$–$C_4$)alkoxy, ($C_1$–$C_4$)alkylthio, ($C_1$–$C_4$)alkylsulfinyl, ($C_1$–$C_4$)alkylsulfonyl, [($C_1$–$C_4$)alkyl]carbonyl, [($C_1$–$C_4$)alkoxy]carbonyl, ($C_3$–$C_6$)cycloalkyl, phenyl, where each of the last-mentioned 8 radicals is unsubstituted or substituted by one or more radicals selected from the group consisting of halogen, ($C_1$–$C_4$)alkoxy, ($C_1$–$C_4$)alkylthio and, in the case of cyclic radicals, also ($C_1$–$C_4$)alkyl and ($C_1$–$C_4$)haloalkyl, or ($C_3$–$C_6$)cycloalkyl which is unsubstituted or substituted by one or more radicals selected from the group consisting of halogen, hydroxyl, cyano, nitro, thiocyanato, formyl, ($C_1$–$C_4$)alkyl, ($C_1$–$C_4$)alkoxy, ($C_1$–$C_4$)alkylthio, ($C_1$–$C_4$)alkylsulfinyl, ($C_1$–$C_4$)alkylsulfonyl, [($C_1$–$C_4$)alkyl]carbonyl, [($C_1$–$C_4$)alkoxy]carbonyl, ($C_2$–$C_4$)alkenyl, ($C_2$–$C_4$)alkynyl, ($C_3$–$C_6$)cycloalkyl, phenyl, where each of the last-mentioned 11 radicals is unsubstituted or substituted by one or more radicals selected from the group consisting of halogen, ($C_1$–$C_4$)alkoxy, ($C_1$–$C_4$)alkylthio and, in the case of cyclic radicals, also ($C_1$–$C_4$)alkyl and ($C_1$–$C_4$)haloalkyl, and
$R^2$,$R^3$ in each case independently of one another are hydrogen, amino, ($C_1$–$C_6$)alkyl, ($C_1$–$C_4$)alkylamino, di[($C_1$–$C_4$)alkyl]amino, ($C_1$–$C_4$)alkyloxy, ($C_3$–$C_6$)cycloalkyl, [($C_1$–$C_4$)alkyl]carbonyl, [($C_1$–$C_4$)alkoxy]carbonyl, phenylcarbonyl, phenoxycarbonyl, ($C_1$–$C_4$)alkylsulfonyl, phenylsulfonyl or a saturated heterocyclyl radical having 3 to 6 ring atoms and 1 to 3 hetero ring atoms selected from the group consisting of N, O and S, where phenyl in the abovementioned radicals or the heterocyclyl radical independently of one another are unsubstituted or substituted by one or more radicals selected from the group consisting of halogen, hydroxyl, ($C_1$–$C_4$)alkoxy, ($C_1$–$C_4$)alkyl, and ($C_1$–$C_4$)haloalkyl, or $R^2$,$R^3$ together with the nitrogen atom of the group $NR^2R^3$ is a saturated heterocyclic radical which has 3 to 6 ring atoms and 1 to 3 hetero ring atoms, where, in addition to the nitrogen atom, the other hetero ring atoms which may be present are selected from the group consisting of N, O and S and the heterocycle is unsubstituted or substituted by one or more radicals selected from the group consisting of halogen, hydroxyl, ($C_1$–$C_4$)alkoxy, ($C_1$–$C_4$)alkyl and ($C_1$–$C_4$)haloalkyl.

3. The process as claimed in claim 1, wherein a chlorinating agent selected from the group consisting of chlorine, salts of hypochlorous acid, phosphorus pentachloride, phosphoryl chloride and thionyl chloride is employed.

4. The process as claimed in claim 1, wherein the chlorinating agent is employed in an amount of 1 to 100 equivalents based on the compound of the formula (II).

5. The process as claimed in claim 1, which is carried out in the presence of an aprotic or essentially anhydrous protic solvent or mixtures of these.

6. The process as claimed in claim 5 which is carried out at temperatures between −40° C. and the boiling point of the solvent or mixtures of solvents employed.

7. The process as claimed in claim 1, which is carried out at temperatures between 0° C. and 50° C.

8. The process as claimed in claim 1, wherein said essentially anhydrous protic solvent is a carboxylic acid.

9. The process as claimed in claim 1, wherein said essentially anhydrous protic solvent is selected from the group consisting of formic acid, acetic acid, n-propionic acid, n-butanoic acid and isobutanoic acid.

10. The process as claimed in claim 1, wherein said essentially anhydrous protic solvent is glacial acetic acid.

11. The process as claimed in claim 1, wherein X is ($C_1$–$C_4$)alkyl.

12. The process as claimed in claim 1, wherein $R^1$ is ($C_1$–$C_6$)alkyl which is unsubstituted or substituted by one or more radicals selected from the group consisting of halogen, hydroxy, methoxy, ethoxy and cyclopropyl.

13. The process as claimed in claim 1, wherein $R^1$ is ($C_3$–$C_6$)cycloalkyl which is unsubstituted or substituted by one or more radicals selected from the group consisting of halogen, hydroxyl, ($C_1$–$C_4$)alkoxy, ($C_1$–$C_4$)alkyl and ($C_1$–$C_4$)haloalkyl.

14. The process of claim 1, wherein X is ($C_1$–$C_4$)alkyl, benzyl or phenyl, where each of the last-mentioned two groups is unsubstituted in the phenyl moiety or substituted by one or more radicals selected from the group consisting of halogen, cyano, nitro, ($C_1$–$C_4$)alkyl, ($C_1$–$C_4$)haloalkyl, ($C_1$–$C_4$)alkoxy, ($C_1$–$C_4$)haloalkoxy and ($C_1$–$C_4$)alkylthio.

15. The process as claimed in claim 1, wherein:
$R^1$ is ($C_1$–$C_6$)alkyl which is unsubstituted or substituted by one or more radicals selected from the group consisting of halogen, hydroxy, methoxy, ethoxy and cyclopropyl; or $R^1$ is $(C_3-C_6)$cycloalkyl which is unsubstituted or substituted by one or more radicals selected from the group consisting of halogen, hydroxyl, $(C_1-C_4)$alkoxy, $(C_1-C_4)$alkyl and $(C_1-C_4)$haloalkyl;

X is $(C_1-C_4)$alkyl, benzyl or phenyl, where each of the last-mentioned two groups is unsubstituted in the phenyl moiety or substituted by one or more radicals selected from the group consisting of halogen, cyano, nitro, $(C_1-C_4)$alkyl, $(C_1-C_4)$haloalkyl, $(C_1-C_4)$alkoxy, $(C_1-C_4)$haloalkoxy and $(C_1-C_4)$alkylthio;

the chlorinating agent is selected from the group consisting of chlorine, salts of hypochlorous acid, phosphorus pentachloride, phosphoryl chloride and thionyl chloride, wherein the chlorinating agent is employed in an amount of 1 to 100 equivalents based on the compound of formula (II); and the essentially anhydrous protic solvent is a carboxylic acid.

16. The process as claimed in claim 15, wherein $R^2$ and $R^3$ are in each case independently of one another are hydrogen, acetyl, amino or methyl.

17. A process for the preparation of a herbicidal aminotriazine of the formula (IV) or a salt thereof:

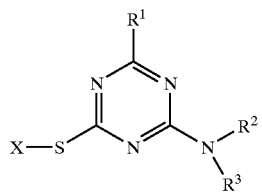
(II)

which comprises chlorinating a 2-amino-4-thio-1,3,5-triazine of the formula (II):

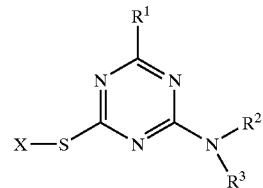
(II)

to give a compound of the formula (I):

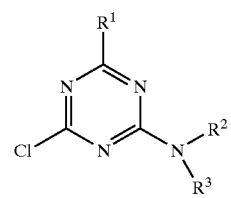
(I)

and reacting the resulting compound of the formula (I) with an amine of the formula (III):

A—NH—R (III)

to give the herbicidal aminotriazine of the formula (IV), where in formulae (I), (II), (III) and (IV), the radicals $R^1$, $R^2$, $R^3$ and X are as defined in claim 1 and A and R are organic radicals which in conjunction with the residual molecular structure of the formula (IV) constitute the chemical structure of a herbicidally active aminotriazine.

18. The process as claimed in claim 17, wherein A is a $(C_1-C_6)$alkylene chain which is substituted in the α-position relative to the amino group by an unsubstituted or substituted alkyl radical and in the ω-position by an optionally substituted aryl, heteroaryl, aryloxy or heteroaryloxy radical and which is further unsubstituted or substituted further with substituents selected from the group consisting of halogen, alkyl, alkoxy and hydroxyl, and R is hydrogen or alkyl.

* * * * *